US00PP11148P

United States Patent [19]

Kordes

[11] Patent Number: Plant 11,148

[45] Date of Patent: Dec. 7, 1999

[54] MINIATURE ROSE PLANT NAMED 'KORHOMAPO'

[75] Inventor: Wilhelm Kordes, Sparrieshoop, Germany

[73] Assignee: Bear Creek Gardens, Inc., Medford, Oreg.

[21] Appl. No.: 09/046,392

[22] Filed: Mar. 23, 1998

[51] Int. Cl.[6] ..... A01H 5/00

[52] U.S. Cl. ..... Plt./129

[58] Field of Search ..... Plt./150, 151, 122, Plt./129

*Primary Examiner*—Howard J. Locker

*Attorney, Agent, or Firm*—Klarquist, Sparkman Campbell, Leigh & Whinston, L.L.P.

[57] ABSTRACT

Miniature rose plant having a compact miniature rose with bright flower color; long shelf life; free flowering qualities; ability to grow rapidly and root easily from softwood cuttings; and have good disease resistance.

1 Drawing Sheet

The present invention relates to a new and distinct variety of rose plant of the miniature class which was originated by me by crossing an unnamed seedling, with an unnamed seedling.

The primary objective of this breeding was to produce a new miniature rose variety having a compact miniature habit with bright flower color; long shelf life; free flowering qualities; ability to grow rapidly and root easily from softwood cuttings; and good disease resistance. The objective was substantially achieved, along with other desirable improvements, as evidenced by the following unique combination of characteristics that are outstanding in the new variety and that distinguish it from its parents, as well as from all other varieties of which I am aware:

1. Roots easily from softwood cuttings;
2. Grows rapidly and flowers quickly;
3. Long shelf life;
4. Bright red, color stable flowers;
5. Good resistance to powdery mildew and rust;
6. Compact, vigorous plant.

'KORhomapo' was selected as an excellent pot rose because of its long shelf life, easy softwood rooting and vigorous growth. It also flowers quickly from cuttings. Potted plants have a shelf life after four days shipping of a minimum of 16–18 days.

Asexual reproduction of this new variety by cutting propagation, as performed at Sparrieshoop, Germany, and Wasco and Somis, Calif. shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character The following is a detailed description of my new rose cultivar with color descriptions using terminology in accordance with the The Royal Horticultural Society (London) Colour Chart, except where ordinary dictionary significance of color is indicated.

Parentage:

*Seed parent.*—Unnamed seedling (unpatented).

*Pollen parent.*—Unnamed seedling (unpatented).

Classification:

*Botanical.*—Rosa hybrida.

*Commercial.*—Miniature rose.

FLOWER

Observations made from specimens grown in a greenhouse environment at Sparrieshoop, Germany and at Somis, Calif. from January, 1996 to December, 1997.

Blooming habit: Continous.

Bud:

*Size.*—Three-fourths inch when the petals start to unfurl.

*Form.*—The bud form is long, blunt topped.

*Color.*—When sepals first divide, bud color is Red Group 53B. When half blown, the upper sides of the petals are Red Group 45A and the lower sides of the petals are Red Group 53B.

*Sepals.*—Color: Green group 138B. Surface texture: Covered in fine hairs. There are three lightly appendaged sepals. There are two unappendaged sepals with hairy edges.

*Receptacle.*—Color: Yellow-Green Group 146C. Shape: Funnel. Size: Small (7/32"×3/16"). Surface: Smooth with a few fine hairs.

*Peduncle.*—Length: Short (1 to 1¼"). Surface: Smooth with a few glands. Color: Green Group 137A. Strength: Stiff, erect.

Bloom:

*Size.*—Small. Average open size is 2 to 2¼ inches.

*Borne.*—Singly and several together in flat clusters of three to five flowers.

*Stems.*—Short. Average length is about eight to ten inches.

*Form.*—When first open: High centered. Permanence: Flattens, all petals curl.

*Petalage.*—Number of petals under normal conditions: 35–40.

*Color.*—The upper sides of the petals are Red Group 45A. The reverse sides of the petals are Red Group 53B. The base of each petal has a small (3/16"×1/8"), White Group 155B, half moon at the point of attachment. The major color on the upper sides is Red Group 45A.

*Variegations.*—Occasional white streak on petals in the center of the flower.

*Discoloration.*—At the end of the first day: No Change. At the end of the third day: No change. By day eight there is a change to Red Group 45C and then to Red Group 45D by petal drop on day eleven or twelve.

*Fragrance.*—None.

Petals:

*Texture.*—Thick.

*Shape.*—Round.

*Form.*—Tips slightly recurved.

*Arrangement.*—Imbricated. Petaloids in the center are many and small.

*Persistence.*—Petals drop off cleanly before drying.

*Lastingness.*—On the plant: Very long (11–12 days). As a cut flower: Very long (15–16 days).

Reproductive parts:

*Anthers.*—Size: Medium. Quantity: Few. Color: Yellow. Arrangement: Regular around styles mixed with petaloids.

*Filaments.*—Color: Very light pink.

*Pollen.*—Color: Lemon yellow.

*Styles.*—Color. Greenish-white.

*Stigmas.*—Color. Greenish-White.

Plant:

*Form.*—Bush.

*Growth.*—Vigorous; upright; branching; compact. At maturity, height is three feet, width is two and one-half feet in a garden setting in Somis, Calif. When grown as a pot rose in a 6½"×4½" pot, the plant is twelve to fourteen inches in height and twelve inches wide.

Foliage: Number of leaflets on normal mid-stem leaves: Five.

*Size.*—Small (3½" long×2½" wide).

*Quantity.*—Abundant.

*Color.*—New foliage: Upper and lower surfaces: Greyed-Red Group 178B. Old foliage: Upper surface: Green Group 137A. Lower surface: Green Group 137D.

*Shape.*—Pointed oval.

*Texture.*—Upper side. Leathery, glossy.

*Edge.*—Serrated.

*Serration.*—Single, small.

*Petiole rachis.*—Color. Green Group 137C.

*Petiole underside.*—Smooth with occasional prickles.

*Stipules.*—Short (½"), serrated, bearded.

*Disease resistance.*—Resistant to mildew and rust under normal growing conditions at Sparrieshoop, Germany and Somis, Calif.

Wood:

*New wood.*—Color: Green Group 137C. Bark: Smooth.

*Old wood.*—Color: Green Group 137A. Bark: Smooth.

Prickles:

*Quantity.*—On main canes from base: Ordinary. On laterals from main canes: Ordinary.

*Form.*—Short, straight.

*Color when young.*—Greyed-Purple Group 183C.

Small prickles:

*Quantity.*—On main stalks: None. On laterals. None.

I claim:

1. A new and distinct variety of miniature rose plant as herein shown and described characterized particularly as a compact miniature rose with bright flower color; long shelf life; free flowering qualities; ability to grow rapidly and root easily from softwood cuttings; and good disease resistance.

* * * * *

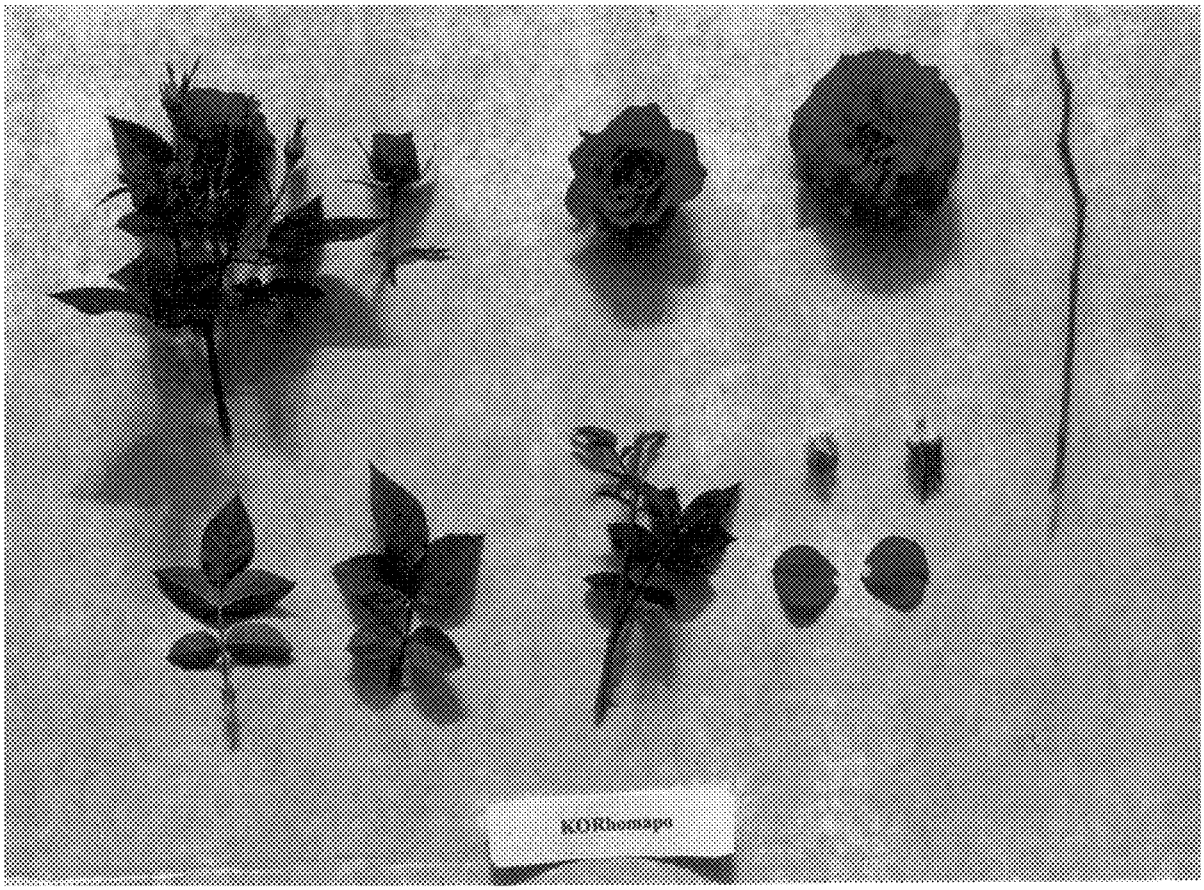
KORlosaps